United States Patent [19]

Lathrop, Jr.

[11] 4,331,633
[45] May 25, 1982

[54] BATCH STERILIZING UNIT
[75] Inventor: Robert L. Lathrop, Jr., San Jose, Calif.
[73] Assignee: FMC Corporation, Chicago, Ill.
[21] Appl. No.: 159,900
[22] Filed: Jun. 16, 1980
[51] Int. Cl.³ .............................................. A61L 2/06
[52] U.S. Cl. ..................................... 422/302; 99/366; 99/483; 422/25; 422/26; 422/297; 426/407
[58] Field of Search .................. 422/25, 26, 296, 297, 422/302, 304; 426/407; 99/366, 467, 470, 483

[56] References Cited
U.S. PATENT DOCUMENTS

| 2,649,380 | 8/1953 | Flynn | 426/407 |
| 3,209,673 | 10/1965 | Howard | 422/302 X |
| 4,228,135 | 10/1980 | Wolff | 422/296 |

FOREIGN PATENT DOCUMENTS 2363468 7/1975 Fed. Rep. of Germany ........ 422/26

*Primary Examiner*—Barry Richman
*Attorney, Agent, or Firm*—Louis J. Pizzanelli; Richard B. Megley

[57] ABSTRACT

A batch sterilizing unit, in the form of a tank having a top loading port and a bottom discharge port, holds a batch of cans for sterilization. The cans in contact with the door associated with the discharge port are prevented from transferring heat to the door and accordingly are maintained at sterilizing temperature by providing a perforated partition forming a wall of condensate sump. Thus the sterilizing medium, whether it be steam or water, is able to effect complete sterilization of those cans making contact with the partition. In addition, condensate is continually discharged from the unit, when steam is the sterilizing medium, insuring creation and maintenance of sterilizing temperatures to the cans resting on the discharge port door.

3 Claims, 6 Drawing Figures

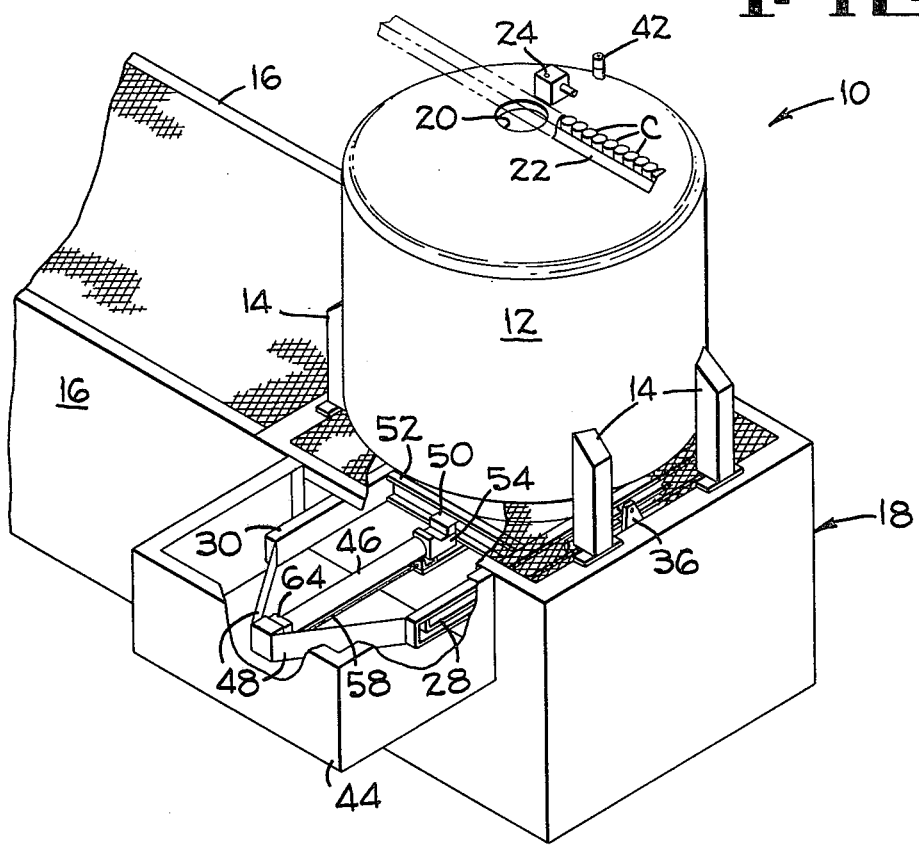
FIG_1
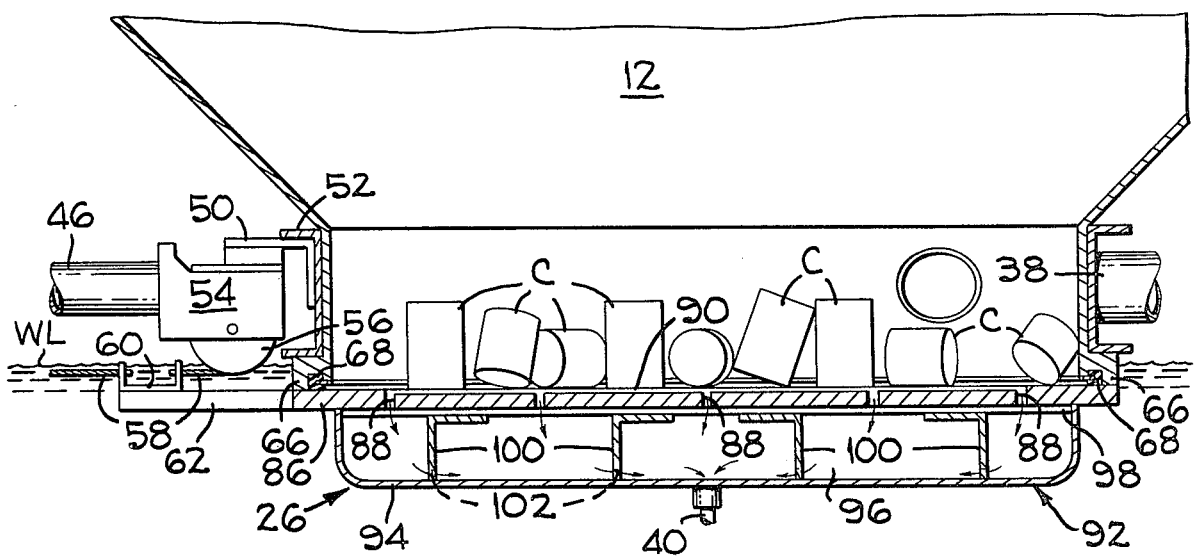
FIG_6

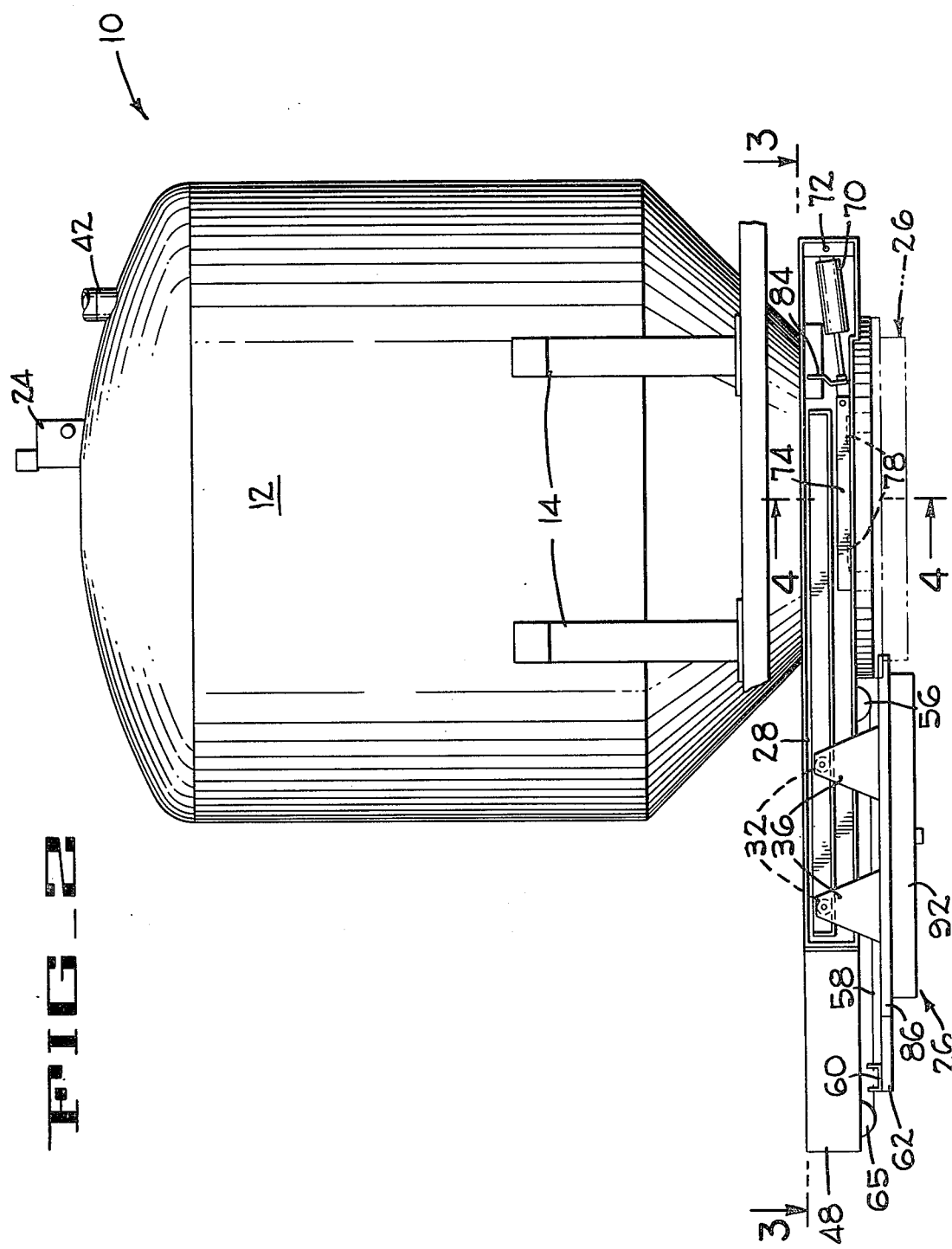

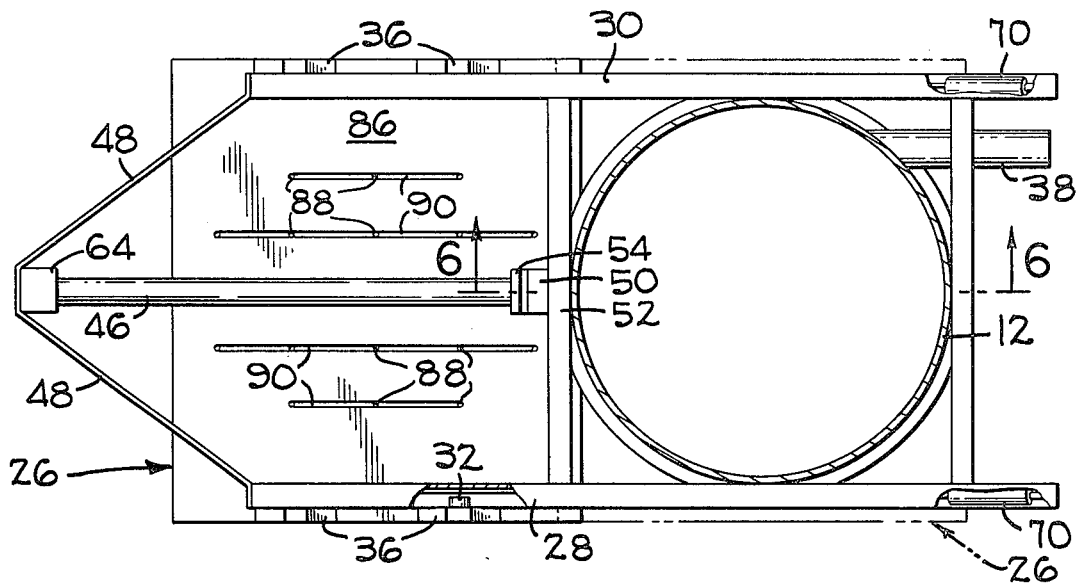
FIG_3
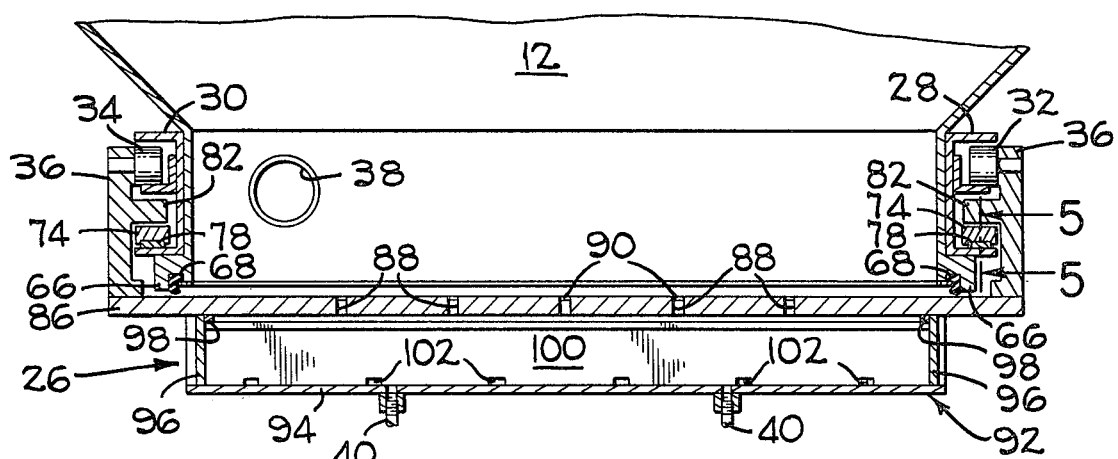
FIG_4
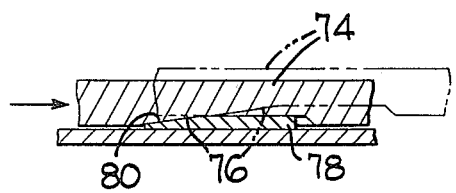
FIG_5

BATCH STERILIZING UNIT

FIELD OF THE INVENTION

The subject matter of this application relates to food sterilizers and more particularly to sterilizers for sterilizing batches of food containers such as cans.

BACKGROUND OF THE INVENTION

Several systems are presently used for sterilizing batches of food packaged in cans. One approach is to dump the cans in a basket such that the cans assume an indiscriminate orientation. On being filled, the basket is introduced into a sealable pressure chamber, horizontal or vertical, whose temperature is raised and controlled for a period of time necessary to effect sterilization.

Another approach to sterilizing batches of cans arranges a group of cans in a single generally circular layer on a perforated metal partition which, together with the cans is deposited in a basket. Several of such layers are contained by the basket which is then introduced into a vertical or horizontal pressure chamber for sterilization.

Another approach involves a vertical chamber having a loading port in its upper surface and a discharge port in its lower surface. When loading, the chamber is filled with water and its discharge port is closed. A plurality of cans are introduced into the loading port and then float downwardly toward the bottom of the chamber through the water which serves substantially to reduce the descent rate and accordingly reduces the impact of the cans with the container and the cans previously introduced. On being filled with cans and after the water is removed, the container is closed and steam is introduced to effect sterilization.

SUMMARY OF THE INVENTION

The present invention is related to sterilizers in which the container is filled with water during its loading phase. In accordance therewith means are provided to reduce the possibility that the cans in contact with the discharge port do not achieve the selected sterilizing temperature. The preferred approach in achieving uniform sterilizing temperature involves the provision of a perforated can supporting plate connected to but spaced from the door closing the discharge port. By this arrangement, the cans in contact with the perforated plate are prevented in transferring heat to the door and thus are able to assume the selected sterilizing temperature. The space between the can supporting perforated plate and the solid plate defines a sump for collecting condensate which is continually discharged through a conduit.

BRIEF DESCRIPTION OF THE DRAWINGS

FIG. 1 is a perspective illustrating the sterilizing unit positioned over a discharge cooling water channel;

FIG. 2 is a side elevation, slightly enlarged, of the batch sterilizing unit illustrating the bottom door and some of the structure for opening and closing the door;

FIG. 3 is a section taken substantially along the line 3—3 of FIG. 2;

FIG. 4 is a greatly enlarged section taken substantially along the line 4—4 of FIG. 2 showing details of the construction of the bottom door and the manner in which it is supported for slidable reciprocating motion;

FIG. 5 is a further enlarged fragmentary portion taken substantially along the lines 5—5 of FIG. 4 illustrating a wedging arrangement for moving the bottom door into pressure contact with the lower seal; and FIG. 6 is an enlarged section taken substantially along the line 6—6 of FIG. 3 illustrating a plurality of cans in contact with the lower perforated plate.

DESCRIPTION OF THE PREFERRED EMBODIMENT

A sterilizing unit incorporating the novel subject matter of this disclosure is shown in FIG. 1 and generally identified by the numeral 10. The sterilizing unit takes the form of a generally cylindrical container 12 supported by a plurality of downwardly extending legs 14 above a cooling water channel 18 having opposed walls 16. The upper wall of the container 12 is provided with a loading port 20 through which a single row of cans C, transported by a conveyor 22, are introduced into the container until a predetermined number of cans have been loaded. While not relevant to the present disclosure, a system utilizing sterilizing units 10 may include several cylindrical containers 12 disposed at regularly spaced intervals over the channel 18 with the conveyor 22 extending along each of the successive containers to sequentially fill each container with a predetermined number of cans. To effect sequential loading, a gate mechanism 24 connected to a counting device sequentially fills each container with a predetermined number of cans. Five or six such containers may be mounted over the water channel and the sequence is such that when the last container is filled, the first container is open to discharge the sterilized cans into the water contained in the channel 18.

In the lower surface of the container 12, a door 26 (FIG. 2) is mounted for reciprocation between an open position (in full outline in FIG. 2) to a closed position (phantom outline also in FIG. 2) and it is guided for reciprocation by guide rails 28 and 30 in which side rollers 32 and 34 are rotatably mounted in opposed pairs of brackets 36, rigidly secured to the door 26.

As mentioned above, when the container 12 is being filled with cans, it is filled with water which serves to greatly reduce the descent rate of the cans as they enter the loading port 20. After the selected number of cans have been introduced in the container 12, the water is discharged through a conduit 38 and condensate bleeder lines 40 connected to the bottom door 26. On being filled with cans, the cushioning water is purged from the container 12 by introducing steam in conduit 42 connected to the top of the container 12. When the water level in the container reaches the midpoint or the lower wall of the conduit 38, a valve in that conduit automatically closes preventing escape of steam while the water remaining in the container is discharged through the conduits 40 which remain open during the sterilizing process.

As shown in FIG. 1, the channel 18, at each position where a sterilizing unit 10 is positioned includes a lateral box-like extension 44, which is in communication with the cooling channel 18, and is provided to contain the door 26 and its operating components at a water level WL, (FIG. 6) which is above the lower extremity of the discharge port. Accordingly, as the cans are discharged from the container 12, at the completion of the sterilizing cycle into the water channel 18, cushioning and accordingly the possible collision between cans is attenuated reducing the possibility of damage. In addition, it should be appreciated that the water in channel 18 is continually in motion developing a current carrying the cans away from the discharge port.

The bottom door 26 is operated to an open and closed position by a cable cylinder 46 having one end secured to braces 48 (FIG. 1) and the other end fixed to the base of the container by an angle iron 50 rigidly connected to a channel 52 embracing the lower end of the container 12. The cable cylinder 46 has the end adjacent the container 12 rigidly connected to a hollow block 54 in which is rotatably mounted a sheave 56 having its periphery grooved to receive a cable 58 having its ends clamped to a bracket 60 being rigidly connected to an extension 62 forming part of the lower door structure 26. The other end of the cylinder 46 is fixed to an outboard hollow block 64 which also rotatably mounts a sheave 65 (FIG. 2). According to this construction, pressure fluid selectively admitted to one or the other end of the cylinder 46 effects opening and closing of the door 26. A cable cylinder found suitable for use in the disclosed sterilizer is made by Tol-O-Matic of Minneapolis, Minnesota and identified as Model 500-2.

As mentioned previously, the bottom door includes spaced brackets 36 rotatably mounting rollers 32 and 34 running in guide rails 28 and 30. In order to seal the door structure 26 to the discharge port of the container 12, the lower end of the container is formed with a flange 66 provided with a circumferential groove in which is seated a deformable rubber gasket 68. When the door is fully closed (the phantom outline position of FIG. 2) a switch is activated energizing a circuit which opens a valve to admit pressure hydraulic fluid to the rod ends of actuators 70 having its head end pivotally connected at 72 to the guide rails 28 and 30 and the rod end connected to a bar 74 (FIG. 5) formed with longitudinally spaced camming surfaces 76. The lower web of the channel shaped guide rails 28 and 30 have rigidly connected thereto longitudinally spaced narrow blocks 78 formed with an inclined surface 80 corresponding in inclination to the camming surface 76 of the bars 74. As shown in phantom outline in FIG. 2, each bar 74 is associated with two blocks 78. When the door is closed and a circuit is energized admitting pressure fluid to the rod ends of the actuator 70, the blocks 74 are moved or translated toward the body of the actuator 70 causing the bars of 74 to be raised upwardly and make contact with inwardly extending ledges 82 formed on each of the brackets 36 (FIG. 4). The door structure 26 is accordingly raised to compress the seal 68 which thereby renders the container 12 air tight. The extent to which the seal 68 is compressed is determined by limit switches (not shown) actuated by an arm 84 connected to and extending transversely of the rod of the actuator 70.

In accordance with the principle feature of the present invention, the bottom door structure 26 is made to define a chest or cavity, having an area substantially equal to the area of the discharge port and, in communication with the interior of the chamber or container 12 in which the sterilizing medium (in this particular case steam) under the same thermal conditions is contained in the chest or cavity. Therefore, a construction having these characteristics will subject cans or other packages in contact with the discharge door to substantially the same conditions as any other can or package located within the central region of the container 12. This result follows due to the fact that cans or other packages in contact with the plate defining the wall of the chest achieves the same temperature as the average temperature of the sterilizing medium.

The constructional arrangement of the discharge or bottom door 26 will be explained with reference to FIGS. 4 and 6. It will be seen that the brackets 36 are rigidly connected to a generally rectangular plate 86 having formed therein a plurality of substantially evenly distributed holes 88 which are interconnected by shallow channels 90 which serve to drain condensate from the surface of the plate 86. Attached to and below the plate 86 is a built up structure defining a compartment or chest 92 in communication with the interior of the container 12 by the holes 88. It should be noted that the interior of the chest is connected to condensate drain lines 40 which, as mentioned previously, continually exhaust water and water vapor to the exterior of the container 12.

The chest 92 is made up of a variety of plates and angle irons and includes a bottom plate 94 and side walls 96 affixed to the lower surface of plate 86. At the intersection of the side walls 96 and the plate 86, a spacer element 98 is provided. To lend rigidity to the chest or compartment 92 a plurality of spaced angle irons 100 (FIG. 6) extending transversely to the direction of the guide rails 28 and 30, are provided. The vertical leg of the angles have slots 102 formed therein to permit flow of condensate within the chest 92 and accordingly permit flow through bleeder lines or condensate lines 40.

FIG. 6 shows a representative group of cans C in random orientation resting upon the plate 86. Ruling out the presence of the chest 92, the plate would be in direct contact with the water in the channel 18 and thus stabilize at a temperature which would be lower than the sterilizing temperature in the container 12. Thus, there would be a continual heat transfer across the plate to the water in the channel 18. The cans in contact with the channel 18 would likewise transfer some of their heat to the plate 86 and as a result, and of course, depending upon the area of metal to metal contact between the cans and the channel 18, certain cans in contact with the plate 86 would not reach a uniform sterilizing temperature. However, by providing the chest 92 which is in communication with the sterilizing medium of the container 12, the plate 86 would assume an average temperature substantially equal to the temperature of the sterilizing medium and thus transfer of heat from the cans to the plate 86 would not occur since there would be an absence of a temperature gradient.

Therefore, by providing means for isolating the major surface of the plate 86 from external ambient temperatures, the packages or cans in contact with the bottom door will reach and maintain the predetermined sterilizing temperature.

Although the best mode contemplated for carrying out the present invention has been herein shown and described, it will be apparent that modification and variation may be made without departing from what is regarded to be the subject matter of the invention as defined in the appended claims.

What we claim is:

1. A batch sterilizer having a chamber, said chamber having steam and water connections thereto and said chamber having a lower opening therein through which articles are discharged, and a bottom discharge door for selectively closing said opening, said bottom discharge door comprising, a perforated plate adapted for movement between a first position closing said chamber opening in which said plate on one side constitutes a primary support for articles in said chamber, and a second open position permitting the articles to fall by gravity from said sterilizer chamber, means defining a cavity on one side of said plate remote from said sterilizer chamber, said cavity being defined by an imperforate wall connected to said plate and peripherally embracing said perforations therein, whereby water and steam from said sterilizer chamber may pass through said perforations and into said cavity while said articles remain supported on said plate, said imperforate wall including a drain port in a lower portion thereof defining means for permitting escape of residual water, condensed steam, and steam from said cavity while said articles are supported upon said plate thereby to permit relative equalization of temperatures above and below said plate for uniform treatment of said articles.

2. The sterilizer of claim 1 wherein said plate on said one side includes a plurality of shallow channels therein and intersecting said perforations, thereby to enhance draining of liquids from said plate into said cavity.

3. The sterilizer of claims 1 or 2 wherein said imperforate wall includes a major portion thereof spaced from said plate by a plurality of transversely extending members disposed between said plate and said wall portion.

* * * * *